(12) United States Patent
Houson

(10) Patent No.: US 7,462,731 B2
(45) Date of Patent: Dec. 9, 2008

(54) PROCESSES FOR THE PREPARATION OF HETEROCYCLIC HYDROXYAMINES AND INTERMEDIATES AND CATALYSTS FOR USE THEREIN

(75) Inventor: Ian Nicholas Houson, Huddersfield (GB)

(73) Assignee: NPIL Pharmaceuticals (UK) Limited, Manchester (GB)

( * ) Notice: Subject to any disclaimer, the term of this patent is extended or adjusted under 35 U.S.C. 154(b) by 602 days.

(21) Appl. No.: 10/528,092

(22) PCT Filed: Sep. 12, 2003

(86) PCT No.: PCT/GB03/03982

§ 371 (c)(1),
(2), (4) Date: Mar. 16, 2005

(87) PCT Pub. No.: WO2004/024708

PCT Pub. Date: Mar. 25, 2004

(65) Prior Publication Data

US 2005/0272940 A1    Dec. 8, 2005

(30) Foreign Application Priority Data

Sep. 16, 2002   (GB)   ................. 0221438.5

(51) Int. Cl.
C07F 15/00      (2006.01)
B01J 31/00      (2006.01)
(52) U.S. Cl. .................. 556/137; 502/166; 502/167
(58) Field of Classification Search ............ 556/137; 502/166, 167
See application file for complete search history.

(56) References Cited

U.S. PATENT DOCUMENTS 4,956,388 A    9/1990   Robertson et al. ........... 514/651

(Continued)

FOREIGN PATENT DOCUMENTS

DE    18 16 282    7/1969

(Continued)

OTHER PUBLICATIONS

Ashok Kumar et al.: "A new chemoenzymatic enantioselective synthesis of R-(-)-tomoxetine, ( R)- and (S)—Fluoxetine" Tetrahedron Letters, Elsevier Science Publishers, Amsterdam, NL, vol. 32, No. 16, 1991, pp. 1901-1904, XP002121769 ISSN: 0040-4039 pp. 1902.

(Continued)

Primary Examiner—P. Nazario Gonzalez
(74) Attorney, Agent, or Firm—Morgan Lewis & Bockius LLP

(57) ABSTRACT

A process for the preparation of a compound of Formula (1):

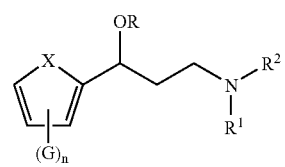

Formula (1)

wherein: X is S, O or $NR^3$, wherein $R^3$ is H or an organic group; R is H or an organic group; $R^1$ and $R^2$ each independently are H, optionally substituted alkyl or optionally substituted aryl; G is a substituent; and n is 0 to 3:
which comprises the steps:
(a) reacting a compound of Formula (2) with a compound of Formula $NHR^1R^2$ to give a compound of Formula (3):

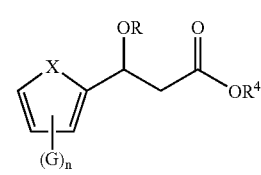

Formula (2)

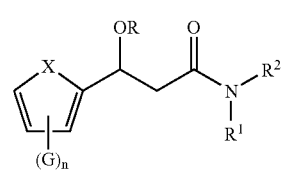

Formula (3)

wherein X, R, G and n are as defined above and $R^4$ is optionally substituted alkyl, optionally substituted alkenyl, optionally substituted alkynyl, optionally substituted aryl, optionally substituted heteroaryl or a combination thereof; and
(b) reducing the compound of Formula (3) to give a compound of Formula (1) is provided.

Processes for the preparation of a compounds of Formula (2), novel compounds of Formula (3) and certain preferred catalysts of formula:

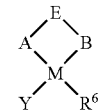

wherein: $R^6$ represents a neutral optionally substituted hydrocarbyl, a neutral optionally substituted perhalogenated hydrocarbyl, or an optionally substituted cyclopentadienyl ligand; A represents an optionally substituted nitrogen; B represents an optionally substituted nitrogen, oxygen, sulphur or phosphorous; E represents a linking group; M represents a metal capable of catalysing transfer hydrogenation; and Y represents an anionic group, a basic ligand or a vacant site; provided that at least one of A or B comprises a substituted nitrogen and the substituent has at least one chiral centre; and provided that when Y is not a vacant site that at least one of A or B carries a hydrogen atom, are also provided.

3 Claims, No Drawings

U.S. PATENT DOCUMENTS

| | | | | |
|---|---|---|---|---|
| 5,023,269 | A | 6/1991 | Robertson et al. | 514/438 |
| 5,362,886 | A | 11/1994 | Berglund | 549/75 |
| 5,491,243 | A | 2/1996 | Berglund | 549/75 |
| 6,184,381 | B1 | 2/2001 | Ikariya et al. | 546/136 |
| 6,723,871 | B2 * | 4/2004 | Tada et al. | 560/184 |

FOREIGN PATENT DOCUMENTS

| | | |
|---|---|---|
| EP | 0 457 559 | 11/1991 |
| EP | 0 654 264 | 5/1995 |
| EP | 916 637 | 5/1999 |
| EP | 1 346 977 | 9/2003 |
| JP | 11-335385 | 12/1999 |
| WO | WO 98/42643 | 10/1998 |
| WO | WO 02/44111 | 6/2002 |

OTHER PUBLICATIONS

Muth, C.W.; et al.: J. Med. Chem., vol. 24, 1981, pp. 1016-1018, XP002267313 scheme II p. 1016, col. 2.

Colwell, W.T.; et al.: J. Med. Chem., vol. 15, No. 7, 1972, pp. 771-775, XP002267314 scheme II p. 772, col. 1.

Miles, W.H.; et al.: Tetrahedron, vol. 57, 2001, pp. 9925-9929, XP002267315 scheme 2 p. 9926.

Harfenist, M.; et al.: J. Am. Chem. Soc., vol. 78, 1956, pp. 1060-1064, XP002267316 p. 1061; figure 1.

Everaere, K.; et al.: Tetrahedron Asymmetry, vol. 10, 1999, pp. 4663-4666, XP002267317 The whole document.

Chemical Abstracts Service, Columbus, Ohio, US; Vogt, Christiane et al: "HPLC Separation of Racemic Amines After Derivatization With (1S)-(+)—Camphor-10-Sulfonylchloride" Retrieved From STN Database Accession No. 114:80674 XP002274379 Abstract & Pharmazie (1990), 45 (9), 691.

Noyori R et al: "Ruthenium (II)- Catalyzed Asymmetric Transfer Hydrogenation of Ketones Using a Formic Acid-Triethylamine Mixture" Journal of the American Chemical Society, American Chemical Society, Washington, DC, US, vol. 118, No. 10, 1996, pp. 2521-2522, XP00240976 ISSN: 0002-7863.

Uematsu N et al: "Asymmetric Transfer Hydrogenation of Imines" Journal of the American Chemical Society, American Chemical Society, Washington, DC, US, vol. 118, No. 20, May 22, 1996, pp. 4916-4917, XP002069432 ISSN: 0002-7863.

Palmer M et al: "(1R,2S)-(+)-cis-1-Amino-2-indanol: an effective ligand for asymmetric catalysis of transfer hydrogenations of ketones" Journal of Organic Chemistry, American Chemical Society, Easton, US, vol. 62, No. 15, Jul. 25, 1997, pp. 5226-5228, XP002150567 ISSN: 0022-3263.

Current Opinion in Investigational Drugs, (PharmaPress Ltd.), 1(1):116-121 (2000).

Deeter et al., "Asymmetric Synthesis and Absolute Stereochemistry of LY248686", Tetrahedron Letters, 31(49):7101-7104 (1990).

Liu et al., "Chemo-Enzymatic Synthesis of the Antidepressant Duloxetine and Its Enantiomer", Chirality, 12:26-29 (2000).

Wheeler et al., "An Asymmetric Synthesis of Duloxetine Hydrochloride, a Mixed Uptake Inhibitor of Serotonin and Norepinephrine, and Its C-14 Labeled Isotopomers", Journal of Labelled Compounds and Radiopharmaceuticals, 36(3):213-233 (1995).

Genet et al., "Practical Asymmetric Hydrogenation of β-Keto Esters at Atmospheric Pressure using Chiral Ru(II) Catalysts", Tetrahedron Letters, 36(27):4801-4804 (1995).

Guerreiro et al., "[RuCl$_2$(COD)]$_n$: A simplified source of Ru(II)-catalysts for the asymmetric hydrogenatoin of functionalized ketones", C.R. Acad. Sci. Paris, 2:175-179 (1999).

Corral et al., "N-Substituted 2-Amino-1-(2-thienyl)ethanols as β-Adrenergic Blocking Agents", Journal of Medicinal Chemistry, 16(8):882-885 (1973).

* cited by examiner

PROCESSES FOR THE PREPARATION OF HETEROCYCLIC HYDROXYAMINES AND INTERMEDIATES AND CATALYSTS FOR USE THEREIN

This invention relates to processes for the preparation of heterocyclic hydroxyamines and to novel substituted heterocycles and catalysts.

Heterocyclic hydroxyamines are important intermediates in the synthesis of many pharmaceuticals. For example Duloxetine ((+)-N-methyl-3-(1-naphthalenyloxy)-2-thiophenepropanamine), a 5-HT and norepinephrine uptake inhibitor, is showing considerable promise as a potential treatment for depression and urinary incontinenance (U.S. Pat. Nos. 5,023,269, 4,956,388 and for a review see Current Opinion in Investigational Drugs (PharmaPress Ltd.) (2000), 1(1), 116-121).

Processes for the manufacture of Duloxetine have been described in Deeter, et al., Tetrahedron Letters, 31(49), 7101-04 (1990); EP654264; U.S. Pat. No. 5,023,269; Liu et al., Chirality, 12(1), 26-29 (2000); EP457559; and Wheeler et al., J. Labelled Compd. Radiopharm, 36(3), 213-223 (1995).

According to the present invention there is provided a process for the preparation of a compound of Formula (1):

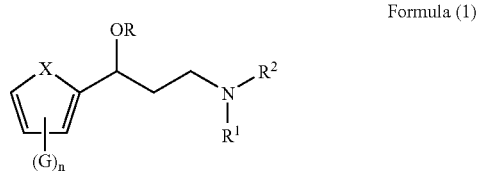

Formula (1)

wherein:
X is S, O or $NR^3$, wherein $R^3$ is H or an organic group;
R is H or an organic group;
$R^1$ and $R^2$ each independently are H, optionally substituted alkyl or optionally substituted aryl;
G is a substituent; and
n is 0 to 3:

which comprises the steps:
(a) reacting a compound of Formula (2) with a compound of Formula $NHR_1R^2$ to give a compound of Formula (3):

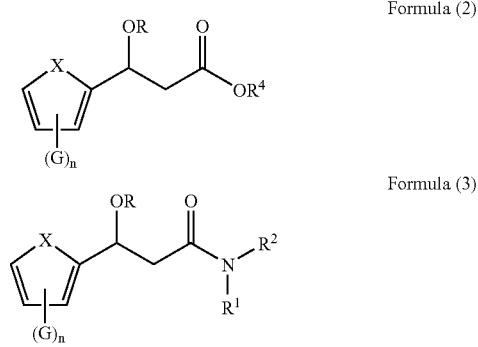

Formula (2)

Formula (3)

wherein X, R, G and n are as defined above and $R^4$ is optionally substituted alkyl, optionally substituted alkenyl, optionally substituted alkynyl, optionally substituted aryl, optionally substituted heteroaryl or a combination thereof; and (b) reducing the compound of Formula (3) to give a compound of Formula (1).

A second aspect of the invention provides a process for the preparation of a compound of Formula (3) whereby a compound of Formula (2) is reacted with a compound of Formula $NHR^1R^2$ to give a compound of Formula (3).

A third aspect of the invention provides a process for the preparation of a compound of Formula (1) in which a compound of Formula (3) is reduced to give a compound of Formula (1).

When X is $NR^3$, then $R^3$ is preferably H, optionally substituted alkyl or optionally substituted aryl, more preferably H or optionally substituted $C_{1-4}$alkyl. It is especially preferred that when X is $NR^3$ then $R^3$ is H.

Preferably X is S.

Preferably n is 0.

Preferably R is H, optionally substituted alkyl, optionally substituted alkenyl, optionally substituted alkynyl, optionally substituted aryl, optionally substituted heterocyclyl or a combination thereof or a hydroxy protecting group such as benzyl, benzoyl or tetrahydropyranyl.

When R is optionally substituted alkyl, optionally substituted alkene or optionally substituted alkyne it may be a linear, branched or cyclic molecule.

It is particularly preferred that R is H; optionally substituted alkyl, especially optionally substituted $C_{1-4}$alkyl; or optionally substituted aryl, especially optionally substituted phenyl or optionally substituted napthyl.

It is especially preferred that R is H or napthyl.

Optional substituents for R are preferably selected from: alkyl (preferably $C_{1-4}$-alkyl), optionally substituted alkoxy (preferably $C_{1-4}$-alkoxy), optionally substituted aryl (preferably phenyl), optionally substituted aryloxy (preferably phenoxy), polyalkylene oxide (preferably polyethylene oxide or polypropylene oxide), carboxy, phosphato, sulpho, nitro, cyano, halo, ureido, —$SO_2F$, hydroxy, ester, —$NR^aR^b$, —$COR^a$, —$CONR^aR^b$, —$NHCOR^a$, carboxyester, sulphone, and —$SO_2NR^aR^b$ wherein $R^a$ and $R^b$ are each independently H or optionally substituted alkyl (especially $C_{1-4}$-alkyl) or, in the case of —$NR^aR^b$, $CONR^aR^b$ and —$SO_2NR^aR^b$, $R^a$ and $R^b$ together with the nitrogen atom to which they are attached represent an aliphatic or aromatic ring system; or a combination thereof.

The substituent G is preferably selected from the optional substituents as for R.

Preferably $R^1$ and $R^2$ are H or optionally substituted $C_{1-4}$alkyl. In a preferred embodiment one of $R^1$ and $R^2$ is H and the other is optionally substituted $C_{1-4}$alkyl. In an especially preferred embodiment one of $R^1$ and $R^2$ is H and the other is methyl.

Optional substituents for $R^1$ and $R^2$ are preferably selected from: optionally substituted alkoxy (preferably $C_{1-4}$-alkoxy), optionally substituted aryl (preferably phenyl), optionally substituted aryloxy (preferably phenoxy), polyalkylene oxide (preferably polyethylene oxide or polypropylene oxide), carboxy, phosphato, sulpho, nitro, cyano, halo, ureido, —$SO_2F$, hydroxy, ester, —$NR^aR^b$, —$COR^a$, —$CONR^aR^b$, —$NHCOR^a$, carboxyester, sulphone, and —$SO_2NR^aR^b$ wherein $R^a$ and $R^b$ are each independently H or optionally substituted alkyl (especially $C_{1-4}$-alkyl) or, in the case of —$NR^aR^b$, $CONR^aR^b$ and —$SO_2NR^aR^b$, $R^a$ and $R^b$ together with the nitrogen atom to which they are attached represent an aliphatic or aromatic ring system; or a combination thereof.

Preferably compounds of Formula (1) prepared by a process according to the invention are of Formula (4):

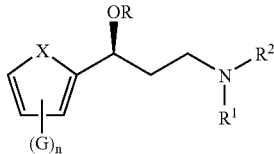

Formula (4)

wherein X, G, n, R, R$^1$ and R$^2$ are as defined above.

In a compound of Formula (2) R$^4$ preferably is optionally substituted alkyl or optionally substituted aryl, more preferably optionally substituted C$_{1-12}$ alkyl or optionally substituted benzyl. It is especially preferred that R$^4$ is optionally substituted C$_{1-4}$ alkyl, particularly ethyl.

Preferred optional substituents for R$^4$ are as for R$^1$ and R$^2$.

Compounds of Formula (2) are preferably formed by acylating a compound of Formula (5):

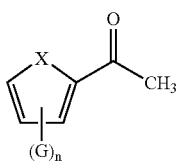

Formula (5)

where X, G and n are as defined above, to give a compound of:

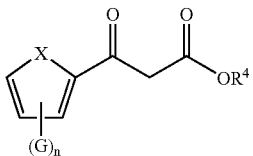

Formula (6)

where X, G, n, and R$^4$ are as defined above, followed by reduction of the Beta-keto group so formed and optionally alkylating the hydroxyl group so formed.

The compound of Formula (5) is preferably acylated by a dialkyl carbonate.

Reduction of the Beta-keto group in compounds of Formula (6) may be carried out by any means known in the art to be able to reduce Beta-keto groups in compounds such as those of Formula (6).

Preferably the reduction of the Beta-keto group in compounds of Formula (6) is achieved by reaction with a hydrogen source other than hydrogen gas. The hydrogen source is preferably formic acid; iso-propanol; cyclohexadiene; an organic formate salt, especially triethylamine or ammonia; an inorganic formate salt, especially potassium, sodium or lithium. More preferrably reduction of the Beta-keto group in compounds of Formula (6) to give a compound of Formula (2) may be by reaction with a mixture a of formic acid and triethylamine, preferably in a molar ratio of formic acid to triethylamine of from 10:1 to 1:1 and especially in a molar ratio of 5:2.

The reduction of the Beta-keto group in compounds of Formula (6) is preferably a stereospecific reduction. The product of this reduction may be either the (S) or the (R) isomer. Preferably the product is produced in at least 80% e.e., more preferably in at least 90% e.e., and especially in at least 95% e.e. Preferably the product of the reduction is a compound of Formula (7):

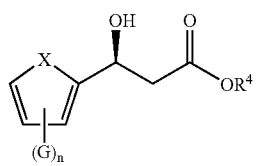

Formula (7)

Where X, G, n and R$^4$ are as defined above.

When reduction of the Beta-keto group in a compound of Formula (6) is a stereospecific reduction it may be carried out by any means known in the art for the stereospecific reduction of Beta-keto groups. These include the use of chemical catalysts (for examples see Genet, J. P.; Ratovelomanana-Vidal, V.; Cano de Andrade, M. C.; Pfister, X.; Guerreiro, P.; Lenoir, J. Y. *Tetrahedron Lett.* 1995, 36, 4801; Guerreiro, P.; Cano de Andrade, M. C.; Henry, J. C.; Tranchier, J. P.; Phansavath, P.; Ratvelomanana-Vidal, V.; Genet, J. P.; Homri, T.; Touati, A. R.; Ben Hassine, B. *C.R. Acad. Sci. Paris*1999, 2, 175; which are incorporated herein by reference; also reactions as described in "Catalytic Asymmetric Synthesis" by Ojima, published by Wiley-VGH (ISBN 0-471-40027-0) and "Principle and Applications of Asymmetric Synthesis by Lin, Li and Chan published by Wiley inter-science (ISBN 0-471-29805-0)) or a biological catalyst such as a whole cell, an enzyme, a cell preparation or a cell free extract.

Preferred catalysts are those asymmetric transfer hydrogenation catalysts which are described in WO97/20789, WO98/42643, and WO02/44111 which are herein incorporated by reference.

Particularly preferred transfer hydrogenation catalysts are those Ru, Rh or Ir catalysts of the type described in WO97/20789, WO98/42643, and WO02/44111 which comprise an optionally substituted diamine ligand, for example optionally substituted ethylene diamine ligands, and a ligand which is selected from the group comprising optionally substituted neutral aromatic ligands, for example p-cymene, and optionally substituted cyclopentadiene ligands. Examples include:

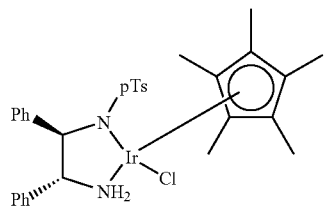

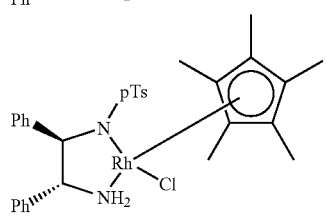

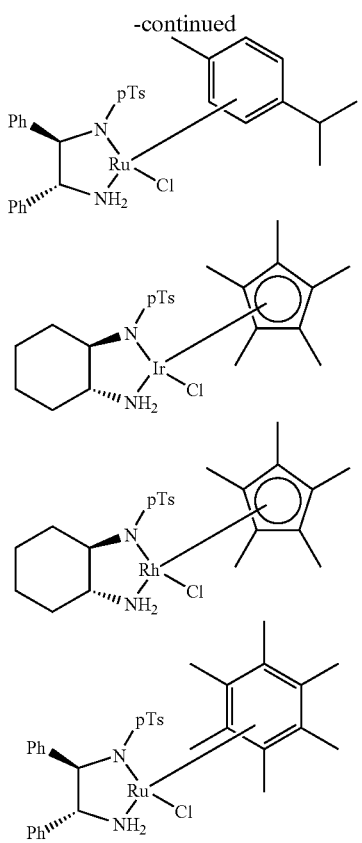

Especially preferred are Ru, Rh or Ir catalysts of the type described in WO97/20789, WO98/142643, and WO02/144111 which comprise an optionally substituted diamine ligand wherein at least one nitrogen atom of the optionally substituted diamine ligand is substituted with a group containing a chiral centre, particularly a sulphonyl group containing a chiral centre.

Most preferred transfer hydrogenation catalysts for use in the process of the present invention have the general formula:

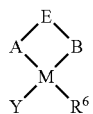

wherein:
$R^6$ represents a neutral optionally substituted hydrocarbyl, a neutral optionally substituted perhalogenated hydrocarbyl, or an optionally substituted cyclopentadienyl ligand;
A represents an optionally substituted nitrogen;
B represents an optionally substituted nitrogen, oxygen, sulphur or phosphorous;
E represents a linking group;
M represents a metal capable of catalysing transfer hydrogenation; and
Y represents an anionic group, a basic ligand or a vacant site;
provided that at least one of A or B comprises a substituted nitrogen and the substituent has at least one chiral centre; and
provided that when Y is not a vacant site that at least one of A or B carries a hydrogen atom.

Preferably, A represents $-NR^7-$, $-NR^8-$, $-NHR^7$, $-NR^7R^8$ or $-NR^8R^9$ where $R^7$ is H, $C(O)R^9$, $SO_2R^9$, $C(O)NR^9R^{13}$, $C(S)NR^9R^{13}$, $C(=NR^{13})SR^{14}$ or $C(=NR^{13})OR^{14}$, $R^8$ and $R^9$ each independently represents an optionally substituted hydrocarbyl, perhalogenated hydrocarbyl or an optionally substituted heterocyclyl group, and $R^{13}$ and $R^{14}$ are each independently hydrogen or a group as defined for $R^9$; and B represents $-O-$, $-OH$, $OR^{10}$, $-S-$, $-SH$, $SR^{10}$, $-NR^{10}-$, $-NR^{11}-$, $-NHR^{11}$, $-NR^{10}R^{11}$, $-NR^{10}R^{12}$, $-PR^{10}-$ or $-PR^{10}R^{12}$ where $R^{11}$ is H, $C(O)R^{12}$, $SO_2R^{12}$, $C(O)NR^{12}R^{15}$, $C(S)NR^{12}R^{15}$, $C(=NR^{15})SR^{16}$ or $C(=NR^{15})OR^{16}$, $R^{10}$ and $R^{12}$ each independently represents an optionally substituted hydrocarbyl, perhalogenated hydrocarbyl or an optionally substituted heterocyclyl group, and $R^{15}$ and $R^{16}$ are each independently hydrogen or a group as defined for $R^{12}$; provided that at least one of A or B comprises a substituted nitrogen and the substituent, represented by $R^7$, $R^8$, $R^9$, $R^{10}$, $R^{11}$ or $R^{12}$, has at least one chiral center.

More preferably, A represents $-NR^7-$, $-NR^8-$, $-NHR^7$, $-NR^7R^8$ or $-NR^8R^9$ where $R^7$ is H, $C(O)R^9$, $SO_2R^9$, $C(O)NR^9R^{13}$, $C(S)NR^9R^{13}$, $C(=NR^{13})SR^{14}$ or $C(=NR^{13})OR^{14}$, $R^8$ and $R^9$ each independently represents an optionally substituted hydrocarbyl, perhalogenated hydrocarbyl or an optionally substituted heterocyclyl group, and $R^{13}$ and $R^{14}$ are each independently hydrogen or a group as defined for $R^9$; and B represents $-NR^{10}-$, $-NR^{11}-$, $-NHR^{11}$, $-NR^{10}R^{11}$, or $-NR^{10}R^{12}$ where $R^{11}$ is H, $C(O)R^{12}$, $SO_2R^{12}$, $C(O)NR^{12}R^{15}$, $C(S)NR^{12}R^{15}$, $C(=NR^{15})SR^{16}$ or $C(=NR^{15})OR^{16}$, $R^{10}$ and $R^{12}$ each independently represents an optionally substituted hydrocarbyl, perhalogenated hydrocarbyl or an optionally substituted heterocyclyl group, and $R^{15}$ and $R^{16}$ are each independently hydrogen or a group as defined for $R^{12}$; provided that at least one of A or B comprises a substituted nitrogen and the substituent, represented by $R^7$, $R^8$, $R^9$, $R^{10}$, $R^{11}$ or $R^{12}$, has at least one chiral center.

Preferably, when either of A or B is present as a group represented by $-NR^7-$, $-NHR^7$, $NR^7R^8$, $-NR^{11}-$, $-NHR^{11}$ or $NR^{10}R^{11}$ wherein $R^8$ and $R^{10}$ are as hereinbefore defined, and where $R^7$ or $R^{11}$ is a group represented by $C(O)NR^9R^{13}$, $C(S)NR^9R^{13}$, $C(=NR^{13})SR^{14}$, $C(=NR^{13})OR^{14}$, $C(O)NR^{12}R^{15}$, $C(S)NR^{12}R^{15}$, $C(=NR^{15})SR^{16}$ or $C(=NR^{15})OR^{16}$, that at least one of $R^9$, $R^{12}$, $R^{14}$, $R^{15}$ or $R^{16}$ is an optionally substituted hydrocarbyl, perhalogenated hydrocarbyl or an optionally substituted heterocyclyl group having at least one chiral center.

More preferably, when either A or B is an amide group represented by $-NR^7-$, $-NHR^7$, $NR^7R^8$, $-NR^{11}-$, $-NHR^{11}$ or $NR^{10}R^{11}$ wherein $R^8$ and $R^{10}$ are as hereinbefore defined, and where $R^7$ or $R^{11}$ is an acyl group represented by $-C(O)R^9$ or $-C(O)R^{12}$, that $R^9$ and $R^{12}$ is an optionally substituted hydrocarbyl, perhalogenated hydrocarbyl or an optionally substituted heterocyclyl group having at least one chiral center. Examples of acyl groups which may be represented by $R^7$ or $R^{11}$ include (R)-2-methyl-2-(4-methylphenyl)ethanoyl; (R)-2-methyl-2-(4-isobutylphenyl)ethanoyl; (R)-2-methyl-2-(6-methoxy-2-naphthyl)ethanoyl; (S)-2-hydroxy-2-(2-chlorophenyl)ethanoyl; and (R)-2-methyl-2-(3-pyridyl)ethanoyl.

Most preferably, when either A or B is present as a sulphonamide group represented by $-NR^7-$, $-NHR^7$, $NR^7R^8$, $-NR^{11}-$, $-NHR^{11}$ or $NR^{10}R^{11}$ wherein $R^8$ and $R^{10}$ are as hereinbefore defined, and where $R^7$ or $R^{11}$ is a sulphonyl group represented by $-S(O)_2R^9$ or $-S(O)_2R^{12}$, that $R^9$ and $R^{12}$ is an optionally substituted hydrocarbyl, perhalogenated hydrocarbyl or an optionally substituted heterocyclyl group having at least one chiral center. Preferred sulphonyl groups include (1R) 1-(7,7-dimethyl-2-oxobicyclo[2.2.1]hept-1-yl)methanesulfonyl, (1S) 1-(7,7-dimethyl-2-oxobicyclo[2.2.1]hept-1-yl)methanesulfonyl, (1R,2S) 1-(7,7-dimethyl-2-hydroxybicyclo[2.2.1]hept-1-yl)methanesulfonyl, (1R,2R) 1-(7,7-dimethyl-2-hydroxybicyclo[2.2.1]hept-1-yl)methanesulfonyl, (1S,2R) 1-(7,7-dimethyl-2-hydroxybicyclo[2.2.1]hept-1-yl)methanesulfonyl, (1S,2S) 1-(7,7-dimethyl-2-hydroxybicyclo[2.2.1]hept-1-yl)methanesulfonyl, (2S) 1-(6,6-dimethylbicyclo[3.1.1]hept-2-ene)-2-ethansulfonyl, (2R) 1-(6,6-dimethylbicyclo[3.1.1]hept-2-ene)-2-ethansulfonyl, (2S) 1-(6,6-dimethylbicyclo[3.1.1]hept-2-ene)-2-methansulfonyl, (2R) 1-(6,6-dimethylbicyclo[3.1.1]hept-2-ene)-2-methansulfonyl, (1R,2R,5R) 5-isopropyl-2-methylcyclohexansulfonyl, and (1S,2S,5R) 5-isopropyl-2-methylcyclohexansulfonyl, (1S,2S,5R) 2-isopropyl-5-methylcyclohexansulfonyl.

It will be recognised that the precise nature of A and B will be determined by whether A and/or B are formally bonded to the metal or are coordinated to the metal via a lone pair of electrons.

Hydrocarbyl groups which may be represented by one or more of $R^{8-10}$ and $R^{12-16}$, include alkyl, alkenyl, alkynyl and aryl groups, and any combination thereof, such as aralkyl and alkaryl, for example benzyl, alpha-methylbenzyl and trityl groups.

Alkyl groups which may be represented by one or more of $R^{8-10}$ and $R^{12-16}$ include linear and branched alkyl groups comprising up to 20 carbon atoms, particularly from 1 to 7 carbon atoms and preferably from 1 to 5 carbon atoms. When the alkyl groups are branched, the groups often comprise up to 10 branched chain carbon atoms, preferably up to 4 branched chain atoms. In certain embodiments, the alkyl group may be cyclic, commonly comprising from 3 to 10 carbon atoms in the largest ring and optionally featuring one or more bridging rings. Examples of alkyl groups which may be represented by $R^{8-10}$ and $R^{12-16}$ include methyl, ethyl, propyl, 2-propyl, butyl, 2-butyl, t-butyl and cyclohexyl groups.

Alkenyl groups which may be represented by one or more of $R^{8-10}$ and $R^{12-16}$ include $C_{2-20}$, and preferably $C_{2-6}$ alkenyl groups. One or more carbon—carbon double bonds may be present. The alkenyl group may carry one or more substituents, particularly phenyl substituents. Examples of alkenyl groups include vinyl, styryl, cyclohexenyl, cyclopentenyl and indenyl groups.

Alkynyl groups which may be represented by one or more of $R^{8-10}$ and $R^{12-16}$ include $C_{2-20}$, and preferably $C_{2-10}$ alkynyl groups. One or more carbon—carbon triple bonds may be present. The alkynyl group may carry one or more substituents, particularly phenyl substituents. Examples of alkynyl groups include ethynyl, propyl and phenylethynyl groups.

Aryl groups which may be represented by one or more of $R^{8-10}$ and $R^{12-16}$ may contain 1 ring or 2 or more fused rings which may include cycloalkyl, aryl or heterocyclic rings. Examples of aryl groups which may be represented by $R^{8-10}$ and $R^{12-16}$ include phenyl, tolyl, fluorophenyl, chlorophenyl, bromophenyl, trifluoromethylphenyl, anisyl, naphthyl and ferrocenyl groups. Perhalogenated hydrocarbyl groups which may be represented by one or more of $R^{8-10}$ and $R^{12-16}$ independently include perhalogenated alkyl and aryl groups, and any combination thereof, such as aralkyl and alkaryl groups. Examples of perhalogenated alkyl groups which may be represented by $R^{8-10}$ and $R^{12-16}$ include —$CF_3$, —$C_2F_5$ and $C_8H_3F_{15}$.

Heterocyclic groups which may be represented by one or more of $R^{8-10}$ and $R^{12-16}$ independently include aromatic, saturated and partially unsaturated ring systems and may comprise 1 ring or 2 or more fused rings which may include cycloalkyl, aryl or heterocyclic rings. The heterocyclic group will contain at least one heterocyclic ring, the largest of which will commonly comprise from 3 to 7 ring atoms in which at least one atom is carbon and at least one atom is any of N, O, S or P. Examples of heterocyclic groups which may be represented by $R^{8-10}$ and $R^{12-16}$ include pyridyl, pyrimidyl, pyrrolyl, thiophenyl, furanyl, indolyl, quinolyl, isoquinolyl, imidazoyl, oxazolyl, piperidinyl, morpholinyl and triazoyl groups.

When any of $R^{8-10}$ and $R^{12-16}$ is a substituted hydrocarbyl or heterocyclic group, the substituent(s) should be such so as not to adversely affect the rate or stereoselectivety of the reaction. Optional substituents include halogen, cyano, nitro, hydroxy, amino, imino, thiol, acyl, hydrocarbyl, perhalogenated hydrocarbyl, heterocyclyl, hydrocarbyloxy, mono or di-hydrocarbylamino, hydrocarbylthio, esters, carboxy, carbonates, amides, sulphonyl and sulphonamido groups wherein the hydrocarbyl groups are as defined for $R^8$ above. One or more substituents may be present. $R^{8-10}$ and $R^{12-16}$ may each contain one or more chiral centres.

The neutral optionally substituted hydrocarbyl or perhalogenated hydrocarbyl ligand which may be represented by $R^6$ includes optionally substituted aryl and alkenyl ligands.

Optionally substituted aryl ligands which may be represented by $R^6$ may contain 1 ring or 2 or more fused rings which include cycloalkyl, aryl or heterocyclic rings. Preferably, the ligand comprises a 6 membered aromatic ring. The ring or rings of the aryl ligand are often substituted with hydrocarbyl groups. The substitution pattern and the number of substituents will vary and may be influenced by the number of rings present, but often from 1 to 6 hydrocarbyl substituent groups are present, preferably 2, 3 or 6 hydrocarbyl groups and more preferably 6 hydrocarbyl groups. Preferred hydrocarbyl substituents include methyl, ethyl, iso-propyl, menthyl, neomenthyl and phenyl. Particularly when the aryl ligand is a single ring, the ligand is preferably benzene or a substituted benzene. When the ligand is a perhalogenated hydrocarbyl, preferably it is a polyhalogenated benzene such as hexachlorobenzene or hexafluorobenzne. When the hydrocarbyl substitutents contain enantiomeric and/or diastereomeric centres, it is preferred that the enantiomerically and/or diastereomerically purified forms of these are used. Benzene, p-cymyl, mesitylene and hexamethylbenzene are especially preferred ligands.

Optionally substituted alkenyl ligands which may be represented by $R^6$ include $C_{2-30}$, and preferably $C_{6-12}$, alkenes or cycloalkenes with preferably two or more carbon—carbon double bonds, preferably only two carbon-carbon double bonds. The carbon—carbon double bonds may optionally be conjugated to other unsaturated systems which may be present, but are preferably conjugated to each other. The alkenes or cycloalkenes may be substituted preferably with hydrocarbyl substituents. When the alkene has only one double bond, the optionally substituted alkenyl ligand may comprise two separate alkenes. Preferred hydrocarbyl substituents include methyl, ethyl, iso-propyl and phenyl. Examples of optionally substituted alkenyl ligands include cyclo-octa-1,5-diene and 2,5-norbornadiene. Cyclo-octa-1,5-diene is especially preferred.

Optionally substituted cyclopentadienyl groups which may be represented by $R^6$ includes cyclopentadienyl groups capable of eta-5 bonding. The cyclopentadienyl group is often substituted with from 1 to 5 hydrocarbyl groups, preferably with 3 to 5 hydrocarbyl groups and more preferably with 5 hydrocarbyl groups. Preferred hydrocarbyl substituents include methyl, ethyl and phenyl. When the hydrocarbyl substitutents contain enantiomeric and/or diastereomeric centres, it is preferred that the enantiomerically and/or diastereomerically purified forms of these are used. Examples of optionally substituted cyclopentadienyl groups include cyclopentadienyl, pentamethyl-cyclopentadienyl, pentaphenylcyclopentadienyl, tetraphenylcyclopentadienyl, ethyltetramethylpentadienyl, menthyltetraphenylcyclopentadienyl, neomenthyl-tetraphenylcyclopentadienyl, menthylcyclopentadienyl, neomenthylcyclopentadienyl, tetrahydroindenyl, menthyltetrahydroindenyl and neomenthyltetrahydroindenyl groups. Pentamethylcyclopentadienyl is especially preferred.

Metals which may be represented by M include metals which are capable of catalysing transfer hydrogenation. Preferred metals include transition metals, more preferably the metals in Group VIII of the Periodic Table, especially ruthenium, rhodium or iridium. When the metal is ruthenium it is preferably present in valence state II. When the metal is rhodium or iridium it is preferably present in valence state I when $R^6$ is a neutral optionally substituted hydrocarbyl or a neutral optionally substituted perhalogenated hydrocarbyl ligand, and preferably present in valence state III when $R^6$ is an optionally substituted cyclopentadienyl ligand Anionic groups which may be represented by Y include hydride, hydroxy, hydrocarbyloxy, hydrocarbylamino and halogen groups. Preferably when a halogen is represented by Y, the halogen is chloride. When a hydrocarbyloxy or hydrocarbylamino group is represented by Y, the group may be derived from the deprotonation of the hydrogen donor utilised in the reaction.

Basic ligands which may be represented by Y include water, $C_{1-4}$ alcohols, $C_{1-8}$ primary or secondary amines, or the hydrogen donor which is present in the reaction system. A preferred basic ligand represented by Y is water.

The groups A and B are connected by a linking group E. The linking group E achieves a suitable conformation of A and B so as to allow both A and B to bond or coordinate to the metal, M. A and B are commonly linked through 2, 3 or 4 atoms. The atoms in E linking A and B may carry one or more substituents. The atoms in E, especially the atoms alpha to A or B, may be linked to A and B, in such a way as to form a heterocyclic ring, preferably a saturated ring, and particularly a 5, 6 or 7-membered ring. Such a ring may be fused to one or more other rings. Often the atoms linking A and B will be carbon atoms. Preferably, one or more of the carbon atoms linking A and B will carry substituents in addition to A or B. Substituent groups include those which may substitute $R^8$, as defined above. Advantageously, any such substituent groups are selected to be groups which do not coordinate with the metal, M. Preferred substituents include halogen, cyano, nitro, sulphonyl, hydrocarbyl, perhalogenated hydrocarbyl and heterocyclyl groups as defined above. Most preferred substituents are $C_{1-6}$ alkyl groups, and phenyl groups.

Most preferably, A and B are linked by two carbon atoms, and especially an optionally substituted ethyl moiety. When A and B are linked by two carbon atoms, preferably one or both of the carbon atoms are substituted or the two carbon atoms linking A and B may comprise part of an aromatic or aliphatic cyclic group, particularly a 5, 6 or 7-membered ring. Such a ring may be fused to one or more other such rings. Particularly preferred are embodiments in which E represents a 2 carbon atom separation and one or both of the carbon atoms carries an optionally substituted aryl group as defined above or E represents a 2 carbon atom separation which comprises a cyclopentane or cyclohexane ring, optionally fused to a phenyl ring.

E preferably comprises part of a compound having at least one stereospecific centre. Where any or all of the 2, 3 or 4 atoms linking A and B are substituted so as to define at least one stereospecific centre on one or more of these atoms, it is preferred that at least one of the stereospecific centres be located at the atom adjacent to either group A or B. When at least one such stereospecific centre is present, it is advantageously present in an enantiomerically purified state.

When B represents —O— or —OH, and the adjacent atom in E is carbon, it is preferred that B does not form part of a carboxylic group.

Compounds which may be represented by A-E-B, or from which A-E-B may be derived by deprotonation, are often substituted aminoalcohols, including substituted 4-aminoalkan-1-ols, substituted 1-aminoalkan-4-ols, substituted 3-aminoalkan-1-ols, substituted 1-aminoalkan-3-ols, and especially substituted 2-aminoalkan-1-ols, substituted 1-aminoalkan-2-ols, substituted 3-aminoalkan-2-ols and substituted 2-aminoalkan-3-ols, and particularly substituted 2-aminoethanols or substituted 3-aminopropanols, or are substituted diamines, including substituted 1,4-diaminoalkanes, substituted 1,3-diaminoalkanes, especially substituted 1,2- or 2,3-diaminoalkanes and particularly substituted ethylenediamines. Further substituted aminoalcohols that may be represented by A-E-B are substituted 2-aminocyclopentanols and substituted 2-aminocyclohexanols, preferably fused to a phenyl ring. Further diamines that may be represented by A-E-B are substituted 1,2-diaminocyclopentanes and substituted 1,2-diaminocyclohexanes, preferably fused to a phenyl ring. When a diamine is represented by A-E-B, preferably at least one amino group is N-sulphonated with a chiral sulphonyl group, preferably camphor sulphonyl. The aminoalcohols or diamines are substituted on nitrogen with a substitutent containing a chiral centre, advantageously the aminoalcohols or diamines are also substituted on the linking group, E, by at least one alkyl group, such as a $C_{1-4}$-alkyl, and particularly a methyl, group or at least one aryl group, particularly a phenyl group.

Specific examples of compounds which can be represented by A-E-B and the protonated equivalents from which they may be derived are:

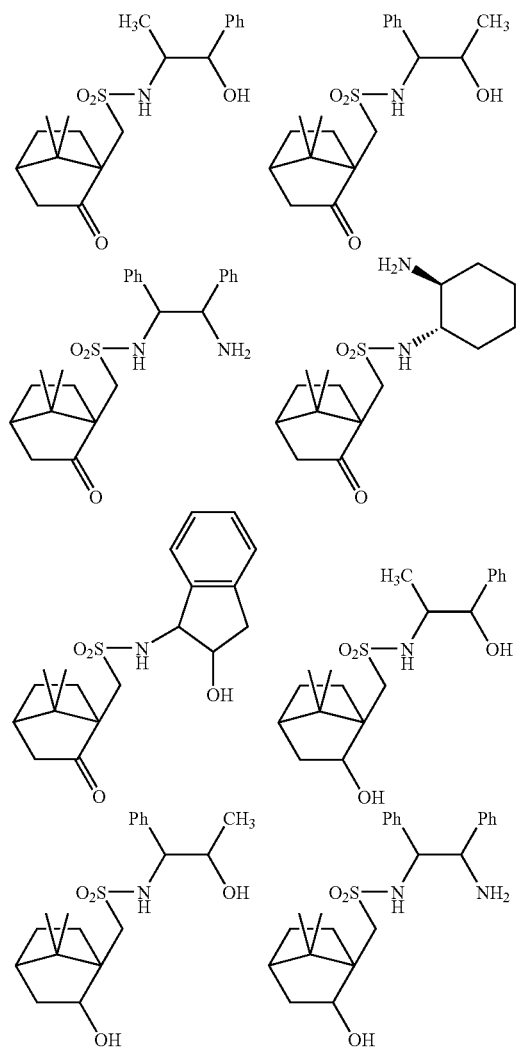

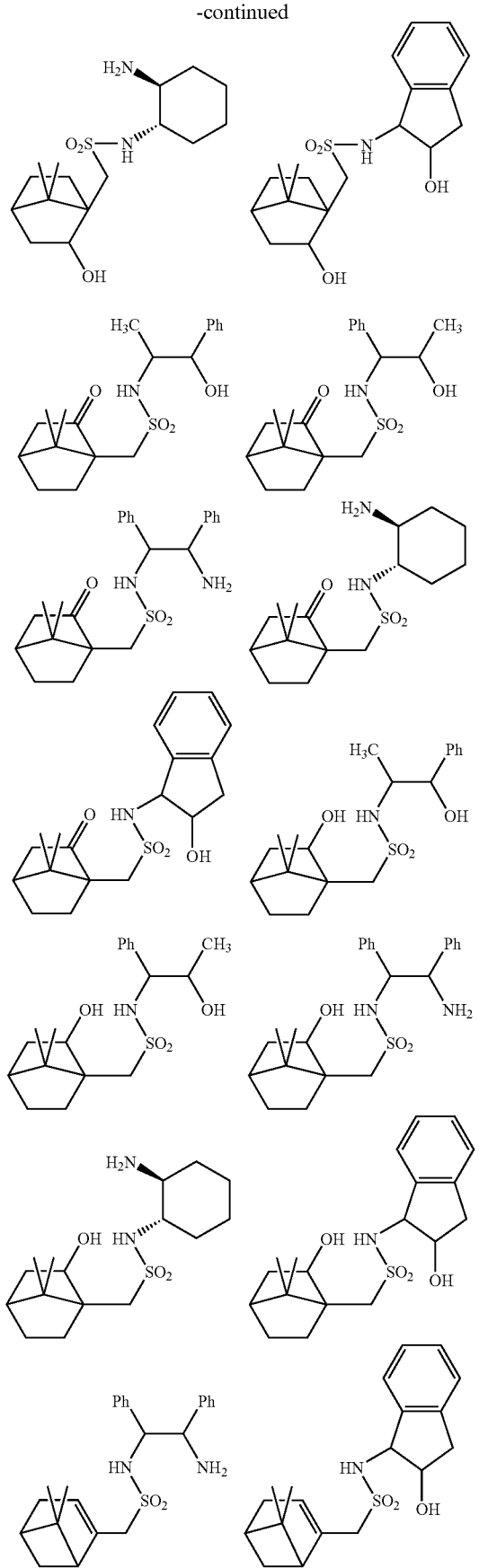
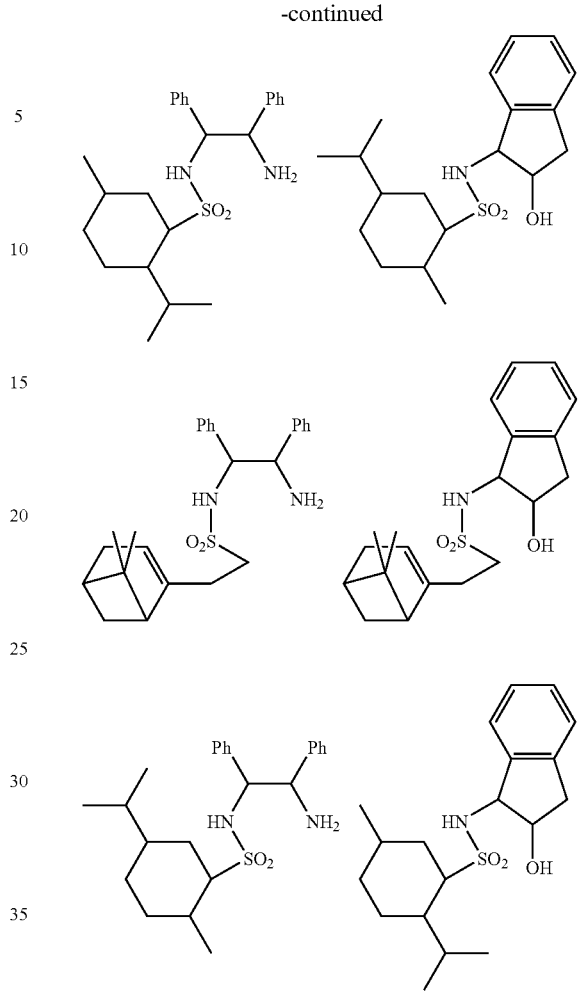

Preferably, the enantiomerically and/or diastereomerically purified forms of these are used. Examples include (1R) 1-(7,7-dimethyl-2-oxobicyclo[2.2.1]hept-1-yl)methanesulfonyl, (1S) 1-(7,7-dimethyl-2-oxobicyclo[2.2.1]hept-1-yl)methanesulfonyl, (1R,2S) 1-(7,7-dimethyl-2-hydroxybicyclo[2.2.1]hept-1-yl)methanesulfonyl, (1R,2R) 1-(7,7-dimethyl-2-hydroxybicyclo[2.2.1]hept-1-yl)methanesulfonyl, (1S,2R) 1-(7,7-dimethyl-2-hydroxybicyclo[2.2.1]hept-1-yl)methanesulfonyl, (1S,2S) 1-(7,7-dimethyl-2-hydroxybicyclo[2.2.1]hept-1-yl)methanesulfonyl(2S) 1-(6,6-dimethylbicyclo[3.1.1]hept-2-ene)-2-ethansulfonyl, (2R) 1-(6,6-dimethylbicyclo[3.1.1]hept-2-ene)-2-ethansulfonyl, (2S) 1-(6,6-dimethylbicyclo[3.1.1]hept-2-ene)-2-methansulfonyl, (2R) 1-(6,6-dimethylbicydo[3.1.1]hept-2-ene)-2-methansulfonyl, (1R,2R,5R) 5-isopropyl-2-methylcyclohexansulfonyl, (1S,2S,5R) 5-isopropyl-2-methylcyclohexansulfonyl, and (1S,2S,5R) 2-isopropyl-5-methylcyclohexansulfonyl.

Most preferably, the nature of A-E-B, $R^6$ and Y are chosen such that the catalyst is chiral. When such is the case, an enantiomerically and/or diastereomerically purified form is preferably employed.

Examples of these preferred catalysts which may be employed in the process of the present invention include:

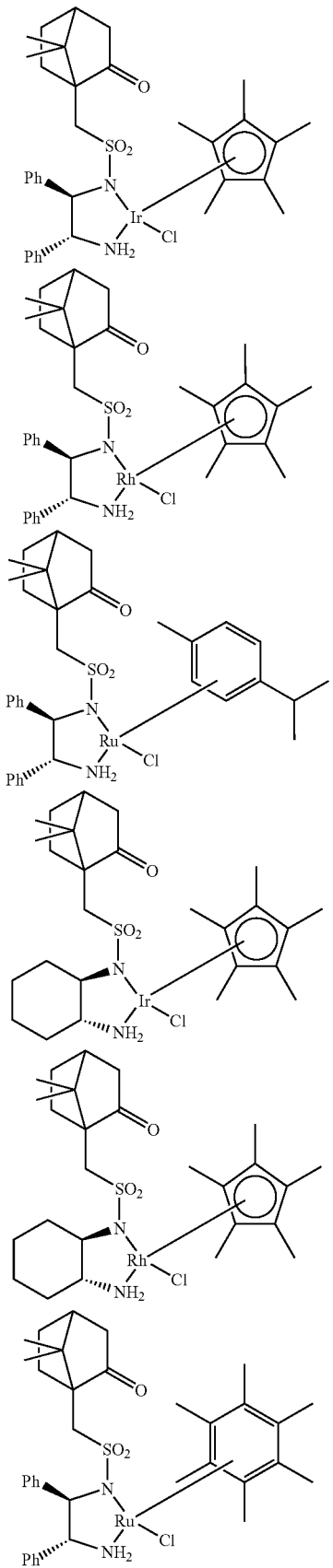

One example of these especially preferred catalysts can be prepared by reacting rhodium pentamethylcyclopentadiene dichloride dimer with (S)-N-camphorsulphonyl-(S,S)-diphenylethylenediamine under the conditions described in Example 6 of WO98/42643 to give a catalyst of Formula:

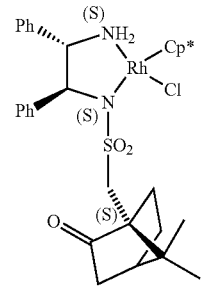

Cp* = Pentamethylcyclopentadiene

Other examples of these especially preferred catalysts include chlororhodium-eta-5-pentamethylcyclopentadienyl N-[(1S,2S)-2-amino-1,2-diphenylethyl]-1-[(1R)-7,7-dimethyl-2-oxobicyclo[2.2.1]hept-1-yl]methanesulfonamide, chlororhodium-eta-5-pentamethylcyclopentadienyl N-[(1R,2R)-2-amino-1,2-diphenylethyl]-1-[(1R)-7,7-dimethyl-2-oxobicyclo[2.2.1]hept-1-yl]methanesulfonamide, chlororhodium-eta-5pentamethylcyclopentadienyl N-[(1S,2S)-2-amino-1,2-diphenylethyl]-1-[(1S)-7,7-dimethyl-2-oxobicyclo[2.2.1]hept-1-yl]methanesulfonamide, chlororhodium-eta-5-pentamethylcyclopentadienyl N-[(1R,2R)-2-amino-1,2-diphenylethyl]-1-[(1S)-7,7-dimethyl-2-oxobicyclo[2.2.1]hept-1-yl]methanesulfonamide, chlororhodium-eta-5-pentamethylcyclopentadienyl N-[(1S,2S)-2-amino-1,2-diphenylethyl]-1-[(1R,2R)-7,7-dimethyl-2-hydroxybicyclo[2.2.1]hept-1-yl]methanesulfonamide, chlororhodium-eta-5-pentamethylcyclopentadienyl N-[(1S,2S)-2-amino-1,2-diphenylethyl]-1-[(1R,2S)-7,7-dimethyl-2-hydroxybicyclo[2.2.1]hept-1-yl]methanesulfonamide, chlororhodium-eta-5-pentamethylcyclopentadienyl N-[(1S,2S)-2-amino-1,2-diphenylethyl]-1-[(1S,2R)-7,7-dimethyl-2-hydroxybicyclo[2.2.1]hept-1-yl]methanesulfonamide, chlororhodium-eta-5-pentamethylcyclopentadienyl N-[(1S,2S)-2-amino-1,2-diphenylethyl]-1-[(1S,2S)-7,7-dimethyl-2-hydroxybicyclo[2.2.1]hept-1-yl]methanesulfonamide, chlororhodium-eta-5-pentamethylcyclopentadienyl N-[(1R,2R)-2-amino-1,2-diphenylethyl]-1-[(1R,2R)-7,7-dimethyl-2-hydroxybicyclo[2.2.1]hept-1-yl]methanesulfonamide, chlororhodium-eta-5-pentamethylcyclopentadienyl N-[(1R,2R)-2-amino-1,2-diphenylethyl]-1-[(1R,2S)-7,7-dimethyl-2-hydroxybicyclo[2.2.1]hept-1-yl]methanesulfonamide, chlororhodium-eta-5-pentamethylcyclopentadienyl N-[(1R,2R)-2-amino-1,2-diphenylethyl]-1-[(1S,2R)-7,7-dimethyl-2-hydroxybicyclo[2.2.1]hept-1-yl]methanesulfonamide, and chlororhodium-eta-5-pentamethylcyclopentadienyl N-[(1R,2R)-2-amino-1,2-diphenylethyl]-1-[(1S,2S)-7,7-dimethyl-2-hydroxybicyclo[2.2.1]hept-1-yl]methanesulfonamide.

The reduction reaction may optionally be carried out under biphasic conditions and is preferably carried out in the absence of oxygen, for example under a nitrogen atmosphere. The preferred temperature range for this reaction is −30 to 90° C., especially 0 to 50° C.

When X is S, preferred compounds of Formula (2), including compounds of Formula (8):

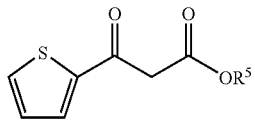

Formula (8)

where $R^5$ is optionally substituted $C_{1-8}$alkyl.

may be prepared by reacting 2-acetyl thiophene with a dialkyl carbonate, more preferably diethyl carbonate, in the presence of a base preferably an alkali salt of the alkyl salt corresponding to the dialkylcarbonate (eg sodium ethoxide if the dialkyl carbonate is diethyl carbonate), a non-nucleophilic base such as NaOtBu, KOtBu, LiOtBu, lithium diisopropylamide, Na, K or Li hexamethyldisylazide, Na in liquid ammonia, sodamide or an amine base with an activating Lewis acid (eg triethylamine with a Mg salt). Especially preferred bases are hydride salts, particularly sodium hydride and non-nucleophilic bases, particularly NaOtBu.

$R^5$ is preferably optionally substituted $C_{1-4}$alkyl and especially ethyl.

The compound of Formula (8) is then preferably reduced by a stereospecific reduction, as described above, to give a compound of Formula (9):

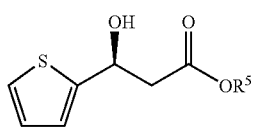

Formula (9)

where $R^5$ is as described above.

The amidation of the compound of Formula (2) in step (a) may be carried out by any means known in the art.

Preferably Step (a) of the process is performed in the presence of any organic solvent or mixture of organic solvents which is unreactive towards the reagents employed. Polar aprotic solvents are especially favoured. Examples of suitable solvents include toluene, tetrahydrofuran, acetonitrile, DMF and ethers.

Step (a) of the invention is preferably carried out in the temperature range of from −20° C. to 150° C. More preferably in the temperature range of from −10° C. to 100° C.

Step (a) of the process is advantageously allowed to proceed to at least 90% and more advantageously at least 95% conversion to a compound of Formula (3).

The reaction time of step (a) of the process of the second aspect of the invention will depend on a number of factors, for example the reagent concentrations, the relative amounts of reagents, the presence of a catalyst, the nature of the solvent and particularly the reaction temperature. Typical reaction times, in addition to the reagent addition times, range from 1 minute to 200 h hours, with reaction times of 5 minutes to 6 hours being common.

When, in a preferred embodiment of the invention, one of $R^1$ and $R^2$ is H and the other is methyl, then step (a) preferably comprises reacting a compound of Formula (2) with methylamine.

It is particularly preferred that the compound of Formula (2) and methylamine are both in solution in either a single or multiphase system.

A preferred solvent system for step (a) comprises water and a water immiscible solvent, especially toluene.

The reduction of the compound of Formula (3) in step (b) may be carried out using any suitable method known in the art. These methods include reduction by: lithium aluminium hydride, di-iso-butylaluminium hydride, lithium borohydride, lithium borohydride with methanol, catecholborane or borane or sodium borohydride preferably with an activating agent such as ethanol, $CH_3SO_2H$, $H_2SO_4$, pyridine, methanol, $TiCl_4$ or $CoCl_2$.

Preferably reduction of the compound of Formula (3) in step (b) is by lithium aluminium hydride.

Step (b) of the process can be performed without any solvent but is preferably performed in the presence of any organic solvent or mixture of organic solvents which is unreactive towards the reagents employed. Examples of suitable solvents include toluene, methanol, hexane, tetrahydrofuran, ethylacetate, octanol, acetonitrile and dimethylformamide. Tetrahydrofuran is especially favoured.

Step (b) of the process is preferably performed in the absence of oxygen. Oxygen may be excluded by, for example, passing an inert gas, especially nitrogen, through the reaction mixture.

Step (b) of the process may be carried out under reduced pressure.

Step (b) of the second aspect of the invention is preferably carried out in the temperature range of from −20° C. to 150° C. and more preferably in the temperature range of from 10° C. to 70° C.

Step (b) of the process of the second aspect of the invention is advantageously allowed to proceed to at least 90% conversion and more preferably to at least 95% conversion, to a compound of Formula (1).

The reaction time of step (b) of the process of the second aspect of the invention will depend on a number of factors, for example the reagent concentrations, the relative amounts of reagents and particularly the reaction temperature. Typical reaction times, in addition to the reagent addition times, range from 1 minute to 200 hours, with reaction times of 2 hours to 48 hours being common.

A preferred embodiment of the present invention provides a process for the preparation of a compound of Formula (10):

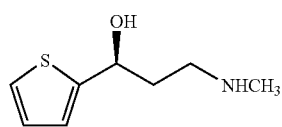

Formula (10)

which comprises the steps:
(a) reacting a compound of Formula (9):

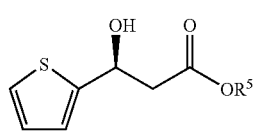

Formula (9)

where $R^5$ is optionally substituted $C_{1-8}$alkyl, with methylamine to give a compound of Formula (11):

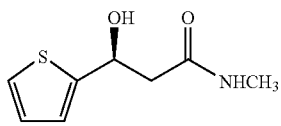

Formula (11)

and
(b) reducing the compound of Formula (11) to give the compound of Formula (10).

The preferred reductant in step (b) is lithium aluminium hydride.

A more preferred embodiment of the present invention provides a process for the preparation of a compound of Formula (10):

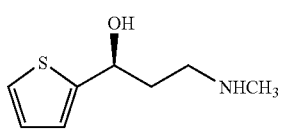

Formula (10)

which comprises the steps:
(i) acetylating 2-acetyl thiophene to give the compound of Formula (8):

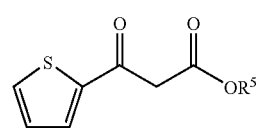

Formula (8)

where $R^5$ is optionally substituted $C_{1-8}$alkyl;
(ii) reducing the compound of Formula (8) to give the compound of Formula (9):

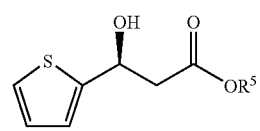

Formula (9)

where $R^5$ is optionally substituted $C_{1-8}$alkyl;
(iii) reacting a compound of Formula (9) with methylamine to give a compound of Formula (11):

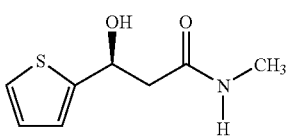

Formula (11)

and
(iv) reducing the compound of Formula (11) to give the compound of Formula (10).
Conditions for steps (i) to (iv) are as described and as preferred above.

According to a fourth aspect of the invention there is provided a compound of Formula (3) as defined above.

In preferred compounds of Formula (3) R and X are as preferred in the first aspect of the invention.

A preferred compound of Formula (3) is of Formula (12):

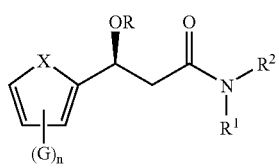

Formula (12)

A more preferred compound of Formula (3) is of Formula (11).

Many of the compounds of Formulae (1) to (12) may exist in the form of a salt. These salts are included within the scope of the present inventions.

The compounds of Formulae (1) to (12) may be converted to the salt form using known techniques.

The compounds of Formulae (1) to (12) may exist in tautomeric forms other than those shown in this specification. These tautomers are also included within the scope of the present inventions.

The invention will now be illustrated, without limitation, by the following examples.

EXAMPLE 1

Stage 1

Preparation of ethyl-3-oxo 3-(2-thiophenyl)propanoate

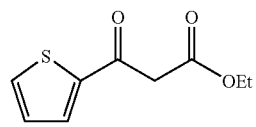

Sodium hydride (60% dispersion in mineral oil, 100 g, 2.5 mol) was washed with anhydrous hexane (2×250 ml) under a nitrogen atmosphere at room temperature. Anhydrous tetrahydrofuran (THF) (340 ml) was then added with stirring followed by 2-acetyl thiophene (136 ml, 1.25 mol) in anhydrous THF (340 ml) over period of 20 minutes. The reaction mixture was then warmed to 35° C. After 30 minutes diethyl carbonate (305.5 ml, 2.5 mol) in anhydrous THF (660 ml) was added over a period of 1 hour. After an additional hour the reaction mixture was cooled to −10° C., quenched with water (475 ml) and glacial acetic acid (145 ml) was added. The mixture was stirred for 20 minutes and then warmed to room temperature. The organic layer was separated and the aqueous layer was extracted with ethyl acetate (3×200 ml). The combined organic extracts were washed with brine (2×200 ml), dried with $Na_2SO_4$ and concentrated under reduced pressure to give the title compound as a crude dark orange oil in 98% yield (242.8 g).

Stage 2

Preparation of ethyl-3-(S)-hydroxy 3-(2-thiophenyl)propanoate

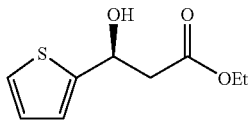

Rhodium pentamethylcyclopentadiene dichloride dimer (1.8705 g, 0.0030 mol) and (S)-N-camphorsulphonyl-(S,S)-diphenylethylenediamine (2.582 g, 0.0061 mol) were stirred in THF (378.5 ml) at 0° C. under nitrogen to form a catalytic solution.

Ethyl-3-oxo 3-(2-thiophenyl)propanoate (300 g, 1.513 mol, from stage 1) was stirred in THF (378.5 ml) at 10° C. and sparged with nitrogen at a rate of 1.2 Lmin$^{-1}$. A portion of the catalytic solution (78.5 ml) was added, and a mixture of formic acid and triethylamine in a molar ratio of 5:2 (327.1 g) was charged at a rate of 52.1 mlhr$^{-1}$. Further portions of the catalytic solution (75 ml) were added every 1.5 hr. After the reaction had been shown to have gone to completion by GC, after about 24 hours, saturated aqueous sodium hydrogen carbonate solution (1 L) was added at room temperature to quench the reaction. The aqueous layer was extracted with toluene (400 ml). The combined organic layers were washed with brine (400 ml, 10% w/w solution) and dried over anhydrous sodium sulphate. The organic solution was concentrated under reduced pressure to give a dark brown oil in 97.5% yield (295.4 g).

Stage 3

Preparation of 3-(S)-hydroxy-N-methyl 3-(2-thiophenyl)propanamide

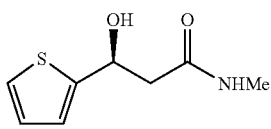

Ethyl-3-(S)-hydroxy 3-(2-thiophenyl)propanoate (270 g, from stage 2) was dissolved in toluene (675 ml). To this, an aqueous methylamine solution (675 ml, 40% w/w) was added with stirring over a period of 15 minutes at room temperature. Once the reaction had gone to completion after 1 hour, agitation was ceased and the organic layer was separated from the aqueous layer. Salt (100 g) was added to the aqueous layer which was then extracted with isopropyl acetate (2×500 ml). The organic extracts and the original organic layer were combined. Silica (250 g) was added and the resulting suspension was stirred for 20 minutes. The mixture was filtered and silica (250 g) was again added and the mixture was stirred for 20 minutes before being filtered. The resulting solution was concentrated under reduced pressure to give orange crystals (90.5 g, 36%) as the product.

Stage 4

Preparation of (S)-3-(N-methyl)amino 1-(2-thiophenyl)propan-1-ol

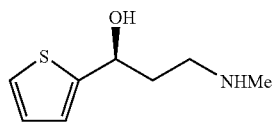

3-(S)-Hydroxy-N-methyl 3-(2-thiophenyl)propanamide (80 g) was dissolved in anhydrous THF (320 ml) under nitrogen with stirring. A solution of lithium aluminium hydride (648 ml, 1 M) in THF was added at rate that kept the temperature constant at 50° C. When all the lithium aluminium hydride solution had been added the reaction mixture was held at 50° C. for 50 minutes. The mixture was then cooled to −10° C. and isopropanol (100 ml) was slowly added. A saturated sodium sulphate solution (310 ml) was then added and the mixture was filtered. The filter residues were washed with ethyl acetate (2×100 ml) and the aqueous layer was separated. The organic layer was washed with saturated brine (2×100 ml) and then dried over sodium sulphate. The organic solution was then concentrated under reduced pressure to give a dark orange oil (65 g, 88%). Solvating the oil in toluene and stirring at 0° C. overnight gave crystals as the final product that were filtered and dried on the filter.

EXAMPLE 2

Preparation of ethyl-3-(S)-hydroxy 3-(2-thiophenyl) propanoate by biological reduction of ethyl-3-oxo 3-(2-thiophenyl)propanoate Yeast cultures were grown on YM (yeast and mold) agar at 28° C. for 72 h. Liquid cultures were prepared by inoculating a single colony from a plate into 50 ml of sterile growth medium consisting of (per litre); glucose (10 g), yeast extract (2 g), trace metal solution (1 ml), $K_2HPO_4$ (1.9 g), $NaH_2PO_4$ $2H_2O$ (2.02 g), $(NH_4)_2SO_4$ (1.8 g), $MgSO_4$ $7H_2O$ (0.2 g) and $FeCl_3$ (0.97 mg) in a 250 ml baffled flask. Following 24 h growth at 28° C. on an orbital shaker, the cells were harvested by centrifuging at 4000 rpm for 10 minutes and the cell pellet was resuspended in 5 ml of 0.1M phosphate buffer, pH 7.5. The cell suspension was centrifuged as above, the supernatant discarded and the cell pellet resuspended in 5 ml of the above buffer. Bioreductions were initiated by the addition of 5 ml of cell suspension to 5 ml of the above buffer containing 4 g/l glucose and 20 ul of ethyl-3-oxo 3-(2-thiophenyl)propanoate from Example 1 stage 1. The cells were incubated for 24 h at 28° C. on an orbital shaker. Formation of ethyl-3-hydroxy 3-(2-thiophenyl) propanoate was monitored by removing 1 ml of cell suspension, centrifuging at 14K rpm for 1 minute to pellet the cells and analysing the supernatant by reverse phase HPLC. Analysis was performed on a Hichrom RPB column (25 cm×4.6 mm i.d.) eluted at 1 ml/min with 0.1% aqueous TFA and acetonitrile (70:30) at a column temperature of 28° C. The reactant and product were detected by their absorbance at 254 nm. The retention time of ethyl-3-oxo 3-(2-thiophenyl)propanoate was 12.7 minutes and the retention time of ethyl-3-hydroxy 3-(2-thiophenyl)propanoate was 9.3 minutes. Bioreduction reactions showing the formation of ethyl-3-hydroxy 3-(2-thiophenyl)propanoate were worked up by centrifuging at 4K rpm for 10 minutes and extracting the supernatant twice with an equal volume of methyl-tert-butylether. The combined extracts were dried over anhydrous sodium sulphate and then the solvent was evaporated to dryness. The residue was taken up in isohexane and 2-propanol (70:30) and the enantiomeric composition of the ethyl-3-hydroxy 3-(2-thiophenyl)propanoate was determined by chiral phase HPLC. Analysis was performed on a Chiralcel OD column (25 cm×4.6 mm i.d. ex Daicel Ltd) eluted at 1 ml/min with isohexane and 2-propanol (90:10) at a column temperature of 28° C. Ethyl-3-oxo 3-(2-thiophenyl)propanoate and the enantiomers of ethyl-3-hydroxy 3-(2-thiophenyl) propanoate were detected by their absorbance at 235 nm. The retention time of ethyl-3-oxo 3-(2-thiophenyl) propanoate was 16.5 minutes, the retention time of ethyl-3-(S)-hydroxy 3-(2-thiophenyl)propanoate was 10.3 minutes and the retention time of ethyl-3-(R)-hydroxy 3-(2-thiophenyl)propanoate was 24.0 minutes. The results are summarised in the following table.

| Microorganism | % Conversion to ethyl-3-(R)-hydroxy 3-(2-thiophenyl) propanoate | % e. e. of (S) enantiomer |
| --- | --- | --- |
| *Saccharomyces carlsbergensis* NCYC398 | 4 | 79 |
| *Hansenula wickerhamii* CBS4307 | 51 | 61 |
| *Saccharomyces cerevisiae* CBS431 | 26 | 80 |
| *Pichia pastoris* CBS704 | 17 | 82 |
| *Debaromyces marama* NCYC282 | 12 | 92 |
| *Hansenula philodendra* CBS6075 | 10 | 91 |
| *Candida intermedia* IFO0761 | 18 | 76 |
| *Pichia angusta* NCYCR320 | 46 | 80 |
| *Candida boidinii* CBS2420 | 66 | 98 |
| *Hansenula nonfermentans* CBS5674 | 65 | 84 |
| *Hansenula angusta* BCC426 | 39 | 93 |
| *Torulopsis* sp. BCC900 | 25 | 78 |
| *Torulopsis molischiana* CBS837 | 64 | 85 |

The invention claimed is:
1. A catalyst of formula:

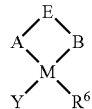

wherein:
R$^6$ represents a neutral optionally substituted hydrocarbyl, a neutral optionally substituted perhalogenated hydrocarbyl, or an optionally substituted cyclopentadienyl ligand;

each of A and B is present as a sulphonamide group represented by —NR$^7$—, —NHR$^7$, NR$^7$R$^8$, —NR$^{11}$—, —NHR$^{11}$ or NR$^{10}$R$^{11}$ wherein R$^8$ and R$^{10}$ are each independently optionally substituted hydrocarbyl, perhalogenated hydrocarbyl or an optionally substituted heterocyclyl group, and where R$^7$ and R$^{11}$ is a sulphonyl group represented by —S(O)$_2$R$^9$ or —S(O)$_2$R$^{12}$, wherein R$^9$ and R$^{12}$ is an optionally substituted hydrocarbyl group which is a cyclic alkyl group comprising from 3 to 10 carbon atoms in the largest ring and optionally including one or more bridging groups;

E represents a linking group;

M represents a metal capable of catalysing transfer hydrogenation; and

Y represents an anionic group, a basic ligand or a vacant site;

provided that when Y is not a vacant site, at least one of A or B carries a hydrogen atom.

2. A catalyst according to claim 1 wherein one of R$^7$ or R$^{11}$ is (1R) 1-(7,7-dimethyl-2-oxobicyclo[2.2.1]hept-1-yl)methanesulfonyl, (1S) 1-(7,7-dimethyl-2-oxobicyclo[2.2.1]hept-1-yl)methanesulfonyl, (1R,2S) 1-(7,7-dimethyl-2-hydroxybicyclo[2.2.1]hept-1-yl)methanesulfonyl, (1R,2R) 1-(7,7-dimethyl-2-hydroxybicyclo[2.2.1]hept-1-yl) methanesulfonyl, (1S,2R) 1-(7,7-dimethyl-2-hydroxybicyclo[2.2.1]hept-1-yl)methanesulfonyl, (1S,2S) 1-(7,7-dimethyl-2-hydroxybicyclo[2.2.1]hept-1-yl)methanesulfonyl, (2S) 1-(6,6-dimethylbicyclo[3.1.1]hept-2-ene)-2-ethansulfonyl, (2R) 1-(6,6-dimethylbicyclo[3.1.1]hept-2-ene)-2-ethansulfonyl, (2S)1-(6,6-dimethylbicyclo[3.1.1]hept-2-ene)-2-methansulfonyl, (2R) 1-(6,6-dimethylbicyclo[3.1.1]hept-2-ene)-2-methansulfonyl, (1R,2R,5R) 5-isopropyl-2-methylcyclohexansulfonyl, or (1S,2S,5R) 5-isopropyl-2-methylcyclohexansulfonyl, (1S,2S,5R) 2-isopropyl-5-methylcyclohexansulfonyl.

3. A catalyst according to claim 1 wherein E is a linking group such that A and B are linked through 2, 3 or 4 atoms which are optionally substituted.

* * * * *